United States Patent [19]

Tilghman

[11] Patent Number: 5,717,992
[45] Date of Patent: Feb. 17, 1998

[54] NOSE GUARD

[76] Inventor: Jane Sanderson Tilghman, 3713 B Greenspring Rd., Havre de Grace, Md. 21078

[21] Appl. No.: 766,489

[22] Filed: Dec. 13, 1996

Related U.S. Application Data

[60] Provisional application No. 60/009,025, Dec. 21, 1995.
[51] Int. Cl.[6] .................................................. A41D 13/00
[52] U.S. Cl. ........................................................ 2/9; 2/206
[58] Field of Search ......................... 2/15, 13, 9, 206, 2/424, 446, 12, 455; 128/857, 858; 351/132, 138, 131

[56] References Cited

U.S. PATENT DOCUMENTS

| | | | |
|---|---|---|---|
| 505,653 | 9/1893 | Gumeson | 2/206 |
| 1,048,191 | 12/1912 | Maurice | 2/9 |
| 1,436,313 | 11/1922 | Hafer | 2/206 |
| 1,582,164 | 4/1926 | Burstyn . | |
| 1,962,818 | 6/1934 | Hoffman . | |
| 2,037,772 | 4/1936 | Everett et al. . | |
| 2,178,800 | 11/1939 | Lombard . | |
| 2,197,973 | 4/1940 | Everett et al. | 2/13 |
| 2,233,698 | 3/1941 | Girouard | 2/206 |
| 2,235,599 | 3/1941 | Woodard . | |
| 2,363,557 | 11/1944 | Schauweker | 2/9 |
| 2,364,354 | 12/1944 | Felch | 2/9 |
| 2,519,561 | 8/1950 | Gillman et al. | 2/206 |
| 2,758,506 | 8/1956 | McNeill | 2/13 |
| 2,870,446 | 1/1959 | Mitchell . | |
| 3,346,875 | 10/1967 | Weisberger . | |
| 4,786,159 | 11/1988 | Piazza, Sr. et al. | 351/158 |
| 5,167,036 | 12/1992 | Daprato | 2/9 |
| 5,274,847 | 1/1994 | Lauttamus | 2/9 |
| 5,416,923 | 5/1995 | Peugh | 2/9 |

*Primary Examiner*—Amy B. Vanatta
*Attorney, Agent, or Firm*—Richard C. Litman

[57] ABSTRACT

A nose guard is disclosed for shielding the nose and central facial region of an individual from excessive exposure to solar radiation. The nose guard is designed for use in conjunction with conventional eyewear. The nose guard has a unitary construction and is secured to the bridge of the eyewear. The nose guard is constructed of soft material capable of conforming to the shape of a nose. The unique design provides solar protection to the nose, while not effecting vision or causing the eyewear to become cumbersome. In preferred embodiments of the invention, the nose guard includes a layer of hypo-allergenic material designed for prolonged contact against skin of the nose.

5 Claims, 2 Drawing Sheets

NOSE GUARD

CROSS REFERENCE TO RELATED APPLICATION

This application claims the benefit of Provisional Patent Application Ser. No. 60/009,025, filed Dec. 21, 1995.

BACKGROUND OF THE INVENTION

1. Field of the Invention

The present invention relates to skin protection devices and more particularly to a device for creating a physical barrier sufficient for protecting skin on the nose from solar radiation.

2. Description of Prior Art

It is well known that the skin on the nose is particularly susceptible to cancer resulting from intense exposure to excessive sunlight. Furthermore, the nose tends to sustain more exposure to sunlight relative to other parts of the body and is thus more likely to become "sun burned". In an attempt to prevent this situation, hats of various kinds have been worn to protect the nose and face from excessive exposure. However, hats are inappropriate for certain outdoor activities such as frisbee or volleyball. Furthermore, hats are ineffective in beach environments where considerable reflected sunlight exists.

It is common practice to apply various ointments and sunscreen lotions to the face and nose to serve as a barrier against sunlight. While generally effective when properly used, there are several drawbacks associated with such ointments and lotions. Some people are allergic to the ingredients contained in the ointment or lotion, thus resulting in uncomfortable skin reactions. On particularly humid days, perspiration can strip away the protective film created by the ointment without the person being aware of it. Finally, if the individual is involved in athletic activities such as frisbee or volleyball, perspiration causes the protection to be quickly lost. Thus, such ointments and lotions only provide limited protection.

In an attempt to overcome some of the disadvantages associated with the use of hats, ointments, and lotions, physical barriers have been utilized to shield the nose from sunlight. These barriers are often in the form of a card or paper which is held in place by wedging it beneath a pair of sunglasses. However, such barriers are unlikely to provide sufficient usefulness over extended periods of time because they can be easily dislodged. Thus the user would constantly need to adjust the barrier. Furthermore, the barrier would need to be repositioned every time the glasses are removed.

The prior art makes various attempts to provide barriers for shielding the nose from sunlight, however most are not aesthetically pleasing. Others are complicated and require an unnecessary amount of time to apply. Still others are only suited for singular use and subsequently provide complications when removal is required. For example, U.S. Pat. No. 1,582,164 issued on Apr. 27, 1923 to Burstyn discloses a face mask for a doctor or dentist. The mask is designed to protect a health care professional's eyes and face from dangerous excretions from the patient during examinations or operations. The face mask is secured by screws to the frames of a pair of eyeglasses.

U.S. Pat. No. 1,962,818 issued on Jun. 12, 1933 to Hoffman discloses a sun shield for the nose. The nose shield is hooked or clamped on to the bridge of a spectacle. The shield may be flat or conform to the shape of the nose.

U.S. Pat. No. 2,037,772 issued on Apr. 21, 1936 to Everett et al. discloses a shield to be used in conjunction with a pair of eyeglasses. The device is supported by the frame of the eyeglasses and designed such that it does not come in contact with the nose.

U.S. Pat. No. 2,178,800 issued on Nov. 7, 1939 to Lombard discloses an inhaler for administering gas to a patient. The inhaler has a nasal hood surrounding the nose. A tube extends over the forehead and the nose to provide gases to the inhaler. The gas tube and the inhaler is secured to the face by being taped to the forehead.

U.S. Pat. No. 2,235,599 issued on Mar. 18, 1941 to Woodard discloses an adjustable eye shield. The eye shield is supported on the head by a head band. The eye shield is hinged so that the user's vision will not be impaired by the shield.

U.S. Pat. No. 2,870,446 issued on Jan. 27, 1959 Mitchell discloses a pilot's instrument flying hood. The hood limits the pilot's vision to the scope of the instrument panel. The hood is used to block the sun's rays from the pilot's vision and allow him or her to fly the airship by monitoring the instrument panel. The hood may be extended to block sunlight from entering the hood near the nose.

U.S. Pat. No. 3,346,875 issued on Oct. 17, 1967 Weisberger discloses a nose and lip protecting apparatus. The apparatus hangs from a pair of eyeglasses and protects the nose and lips from exposure to the elements. The nose protector and the lip protector are detachable, so that they may be used independently of each other.

U.S. Pat. No. 5,167,036 issued on Dec. 1, 1992 to Daprato discloses a nose protector for mounting on eyeglasses. The protector includes a shield for protecting the nose, and channels at each side of the shield for the receiving portion of the eyeglasses. A resilient string member is provided for releasably retaining the portions of the eyeglasses in the channels.

U.S. Pat. No. 5,274,847 issued on Jan. 4, 1994 to Lauttamus discloses a device for attachment to glasses or goggles for protecting a wearer's nose from sunlight. The device is constructed from a single piece of flexible, creaseable material. The device provides a nose shield having a strap extending from its top. The strap is looped over the bridge of the eyewear and threaded through an aperture at the top of the nose shield. The strap also includes locking projections to secure it into place. Once secured, the excess portion of the strap is cut and disposed.

U.S. Pat. No. 5,416,923 issued on May 23, 1995 to Peugh discloses a nose sun shield for eyeglasses which is readily detachable from the glasses. The sun shield is formed from a thin, semi-stiff but thin flexible sheet material. A small piece of hook-and-loop fastening material such as Velcro® is secured to the upper, outer, edge of the sun shield by an adhesive. A corresponding piece of hook-and-eye material is secured by an adhesive to the glasses between the nose pads.

None of the above inventions and patents, taken either singly or in combination, is seen to describe the instant invention as claimed.

SUMMARY OF THE INVENTION

Accordingly, it is a principal object of the invention to provide a device for protecting the nose and central facial region from solar radiation.

It is another object of the invention to provide a device that can be quickly, easily, and securely attached to a pair of eyewear.

It is a further object of the invention to provide a device that can be worn during sporting events while not raising the potential for injury.

It is an object of the invention to provide improved elements and arrangements thereof in an apparatus for the purposes described which is inexpensive, dependable and fully effective in accomplishing its intended purposes.

In accordance with the objects of the invention, a nose guard is provided for shielding the nose and central facial region of an individual from excessive exposure to solar radiation. The nose guard is designed for use in conjunction with conventional eyewear. The term eyewear as used herein refers to any type of eyeglasses or similar device having a pair of lens and a bridge portion for connecting the lens and supporting the eyeglasses upon a person's nose. Examples of such eyewear include prescription glasses, nonprescription glasses, sunglasses, goggles, etc. The nose guard has a unitary construction which allows it to be secured to the bridge of the eyewear. Once secured to the eyewear, the nose guard covers the individual's nose and forms a physical barrier against sunlight. The nose guard is constructed of soft material capable of conforming to the shape of a nose. The soft material also prevents injury if the nose guard is struck by an object such as a ball or frisbee during outdoor activities. The unique design provides solar protection to the nose, while not effecting vision or causing the eyewear to become cumbersome. In preferred embodiments of the invention, the nose guard includes a layer of hypo-allergenic material designed for contacting the skin of the nose.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
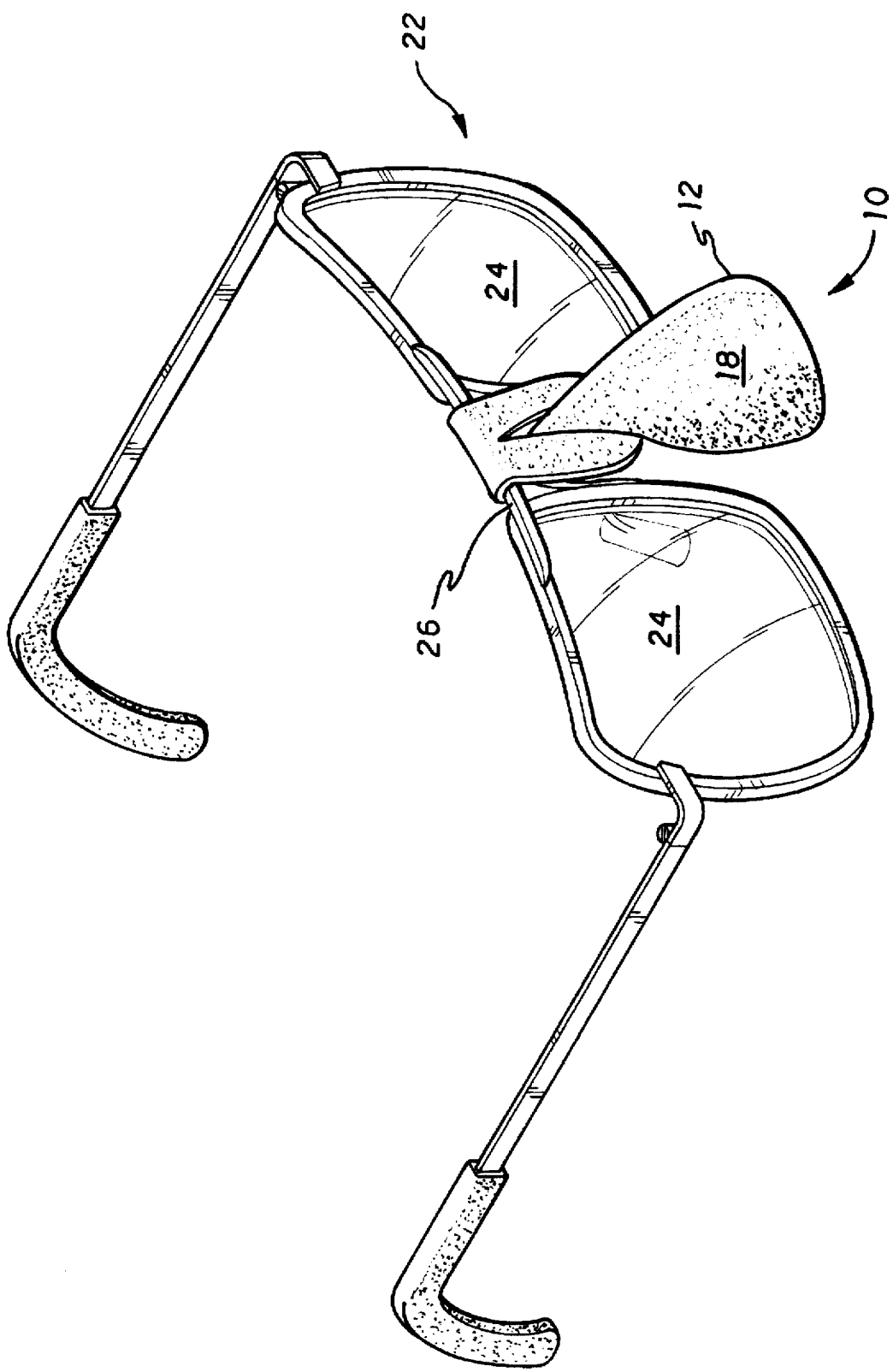
FIG. 1 is a perspective view of the nose guard attached to a pair of eyewear.
Figure 2:
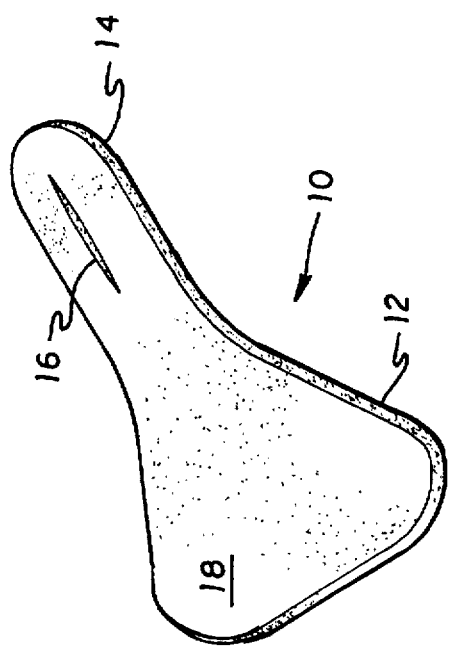
FIG. 2 is a perspective view of the nose guard.
Figure 3:
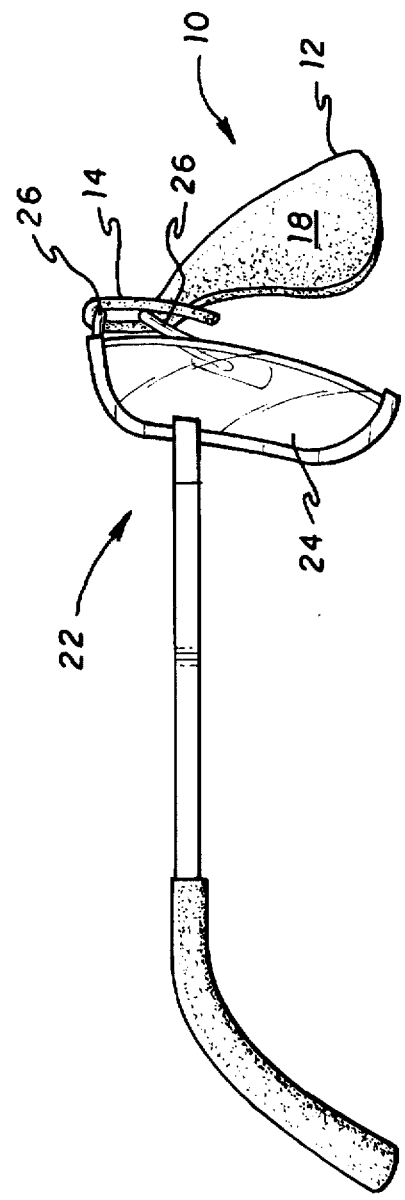
FIG. 3 is a side elevational view of the nose guard attached to the eyewear.

With reference to FIGS. 1–3 a nose guard 10 is shown for protecting the nose and central facial region from excessive exposure to sunlight. The nose guard 10 is helpful in preventing sunburn and skin diseases, such as cancer, which result from overexposure to solar radiation. The nose guard 10 is ideally suited for use by athletes, lifeguards, beach vendors, or similar personnel who are exposed to sunlight for prolonged periods. The nose guard 10 may be constructed from various materials which have flexible properties. As seen in FIGS. 1 and 3, the nose guard 10 is designed for use with conventional eyewear 22. Such eyewear 22 typically include a pair of lens 24 and a bridge 26 structurally interposed between the lens 24. The nose guard 10 is a unitary member which includes a first end 12 and a second end 14. As seen in FIG. 2, the first end 12 of the nose guard 10 is dimensioned substantially greater than the second end 14. The first end 12 functions as the actual physical barrier used to cover the nose and central facial region. While the general shape of the nose guard 10 is illustrated in the figures, the physical dimensions of the first end 12 will depend upon how much of the facial region needs to be protected. Thus, the first end 12 may be designed to cover only the nose or it may be designed to extend outwardly towards the cheeks or possibly downwardly towards the upper lip of the individual.

As seen in FIG. 2, the second end 14 has a generally uniform shape. The second end 14 also contains an aperture 16 which is centrally disposed therein. The aperture 16 is sized such that the first end 12 may pass therethrough when folded. The aperture 16 facilitates attachment of the nose guard 10 to the eyewear 22. The nose guard 10 is attached to the eyewear 22 by looping the first end 12 around the bridge 26 of the eyewear 22. Next, the first end 12 is folded and inserted through the aperture 16. The flexible nature of the nose guard 10 allows the first end 12 to be folded and passed through the aperture 16. In preferred embodiments of the invention, the aperture 16 is disposed in a vertical manner so as to exert a force on the first end 12. This force urges the first end 12 to maintain a pleated fold in the nose guard 10. Thus, the generally flat material of the nose guard 10 is able to conform to the shape of the nose.

The nose guard 10 is designed to protect the user without restricting their physical abilities or senses. It is positioned between the lens 24 of the eyewear 22 such that it does not effect the vision of the user while being worn. It is preferred that the nose guard 10 be constructed from lightweight materials so that significant weight is not added to the eyewear 22. The nose guard 10 does not effect the abilities of the wearer or limit the activities that may be performed while in use. For example, it may be worn during activities such as volleyball or frisbee without fear of being struck, because it's flexible construction is more likely to absorb some of the impact rather than to harm the user. Furthermore the construction of the nose guard 10 assures that it can be quickly and repeatedly placed on and remove from various eyewear 22.

The nose guard 10 can be made of any lightweight material such as foam rubber, foam plastic, cotton, nylon, celluloid, plastic, cardboard, or a combination of materials. In preferred embodiments, the nose guard 10 includes a layer of hypo-allergenic material such as cotton or nylon which is placed in contact with the skin of the nose. The hypo-allergenic material insures that the nose guard 10 may be worn for extended periods of time without discomfort.

In addition to providing a physical barrier from sunlight, the nose guard 10 may be used for various other purposes because it provides a surface which is highly visible to everyone but the person using it. For example, the outer surface 18 of the first end 12 provides an ideal location for placing decorative designs or company trademarks. Thus, the nose guard 10 provides a company a means of advertising their product or trademark in a new manner. Finally, the nose guard 10 supplies a second means of promoting a product for a company because its shape can mirror that of the company's product or trade dress.

It is to be understood that the present invention is not limited to the embodiments described above, but encompasses any and all embodiments within the scope of the following claims.

I claim:

1. Apparatus for protecting the nose comprising:

a flexible member of unitary construction including:
  a first and second end;
  said first end being larger than said second end and merging convergently with said second end;
  said second end having a generally uniform shape and sized for positioning between the lenses of a pair of eyewear, said second end including a slit-like aperture oriented in a vertical manner, said slit-like aperture being appropriately sized for passage of said first end therethrough; whereby said first end is looped around a bridge of the pair of eyewear and inserted through the slit-like aperture, thereby curving said first end to conform to the general shape of a nose and removably securing said flexible member to the pair of eyewear.

2. Apparatus as recited in claim 1 wherein said flexible member comprises a plurality of layers.

3. A protective covering according to claim 2 wherein at least one of said layers comprises a hypo-allergenic material suited for prolonged contact with sensitive skin.

4. A protective covering according to claim 3 wherein said hypo-allergenic material is cotton.

5. A protective covering according to claim 3 wherein said hypo-allergenic material is nylon.

* * * * *